(12) United States Patent
Grossman et al.

(10) Patent No.: US 6,818,441 B1
(45) Date of Patent: Nov. 16, 2004

(54) VECTORS FOR IMPROVING CLONING AND EXPRESSION IN LOW COPY NUMBER PLASMIDS

(75) Inventors: Trudy Grossman, Lexington, MA (US); Ian MacNeil, Milton, MA (US); Paul R. August, Danville, NH (US)

(73) Assignees: Aventis Pharmaceuticals Inc., Bridgewater, NJ (US); Ariad Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 09/596,114

(22) Filed: Jun. 16, 2000

Related U.S. Application Data
(60) Provisional application No. 60/140,287, filed on Jun. 18, 1999.

(51) Int. Cl.[7] .......................... C12N 15/63; C07H 21/04
(52) U.S. Cl. ................... 435/320.1; 536/24.2; 536/23.1
(58) Field of Search ...................... 435/320.1; 536/24.2, 536/23.1

(56) References Cited

U.S. PATENT DOCUMENTS 5,645,991 A * 7/1997 Berg et al.
5,948,622 A * 9/1999 Reznikoff et al.

OTHER PUBLICATIONS

Marsch–Moreno et al. pTn5cat: A Tn5–Derived Genetic Element to facilitate Insertion Mutagenesis, Promoter Probing, Physical Mapping, Cloning, and Marker Exchange in Phytopathogenic and Other Gram–Negative Bacteria Plasmid 39 205–214 1998 Article No. PL9813.*

Berg Clare M. et al., Transposable Elements and the Genetic Engineering of Bacteria, In "Mobile DNA", Berg & Howe Eds, Am. Soc. Microbiology, Washington, DC, 1989, pp. 879–925.

Ioannou Panayiotis A. et al., A New Bacteriophage P1–derived Vector for the Propagation of Large Human DNA Fragments, Nature Genetics vol. 6 Jan. 1994, pp. 84–89.

Osusky Milan et al., Vectors with the fd Replicon for In Vivo Cloning and Analysis of Genes, Gene 151 (1994) 103–108.

Shashikant Cooduvalli S. et al., Recombinogenic Targeting: A New Approach to Genomic Analysis—A Review, Gene 223 (1998) 9–20.

Shizuya Hiroaki et al., Cloning and Stable Maintenance of 300–kilobase–pair Fragments of Human DNA in *Escherichia coli* Using an F–factor–based Vector, Proc. Nat'l. Acad. Sci. USA (1992) vol. 89, pp. 8794–8797.

Healy et al., "Direct Isolation of Genes from the Microbial Community of a Thermophilic Anaerobic Biomass." Abst. Gen.Meet.Am.Soc.Microbiol.; (1994) 94 Meet., 366.

* cited by examiner

*Primary Examiner*—James Ketter
*Assistant Examiner*—Daniel M. Sullivan
(74) *Attorney, Agent, or Firm*—F. Aaron Dubberley

(57) ABSTRACT

Improved vectors and related materials and methods are disclosed.

3 Claims, 11 Drawing Sheets

Amplification of lipase expression from a BAC clone by increasing copy number with pTRANS-SacB

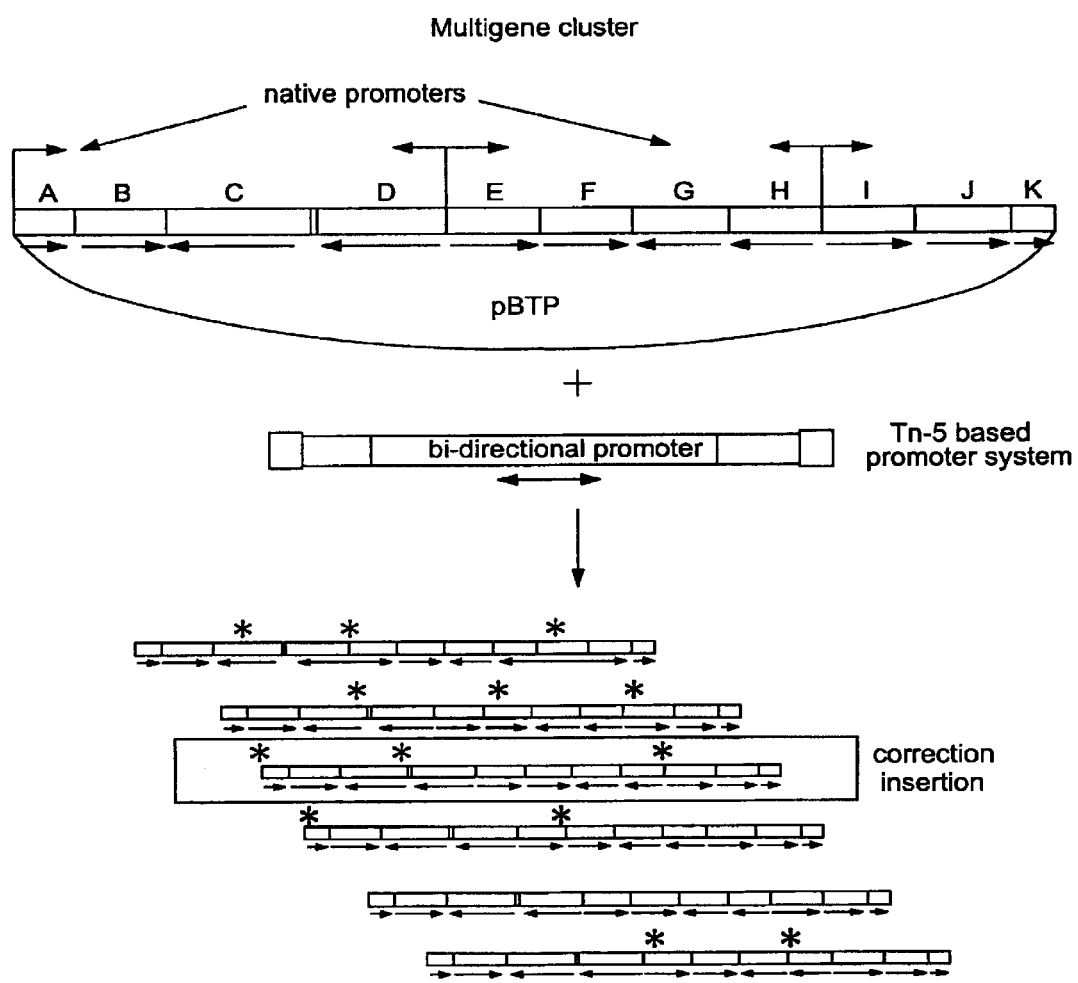

VECTORS FOR IMPROVING CLONING AND EXPRESSION IN LOW COPY NUMBER PLASMIDS

This application claims the benefit of Provisional Application 60/140,287 filed Jun. 18, 1999.

BACKGROUND OF THE INVENTION

Vectors such as cosmids, yeast artificial chromosomes (YACs), and bacterial artificial chromosomes (BACs) permit the construction of large insert genomic DNA libraries. Such libraries have served a pivotal role for the isolation and characterization of important genomic regions and genes from a variety of organisms including bacterial, archaea, mammals etc. The bacterial artificial chromosome (BAC) system is emerging as the system of choice for constructing libraries with DNA inserts up to 300 kilobases. A major advantage of BACs is that plasmids containing large inserts can be efficiently transformed by electroporation and propagated in E. coli. The low copy number of the BAC vector (1–2 per cell), is thought to contribute to the stability of large BACs over many generations, as compared to multi-copy counterparts (Kim et al, NAR, 20(5):1083–1085). The popular BAC vector pBeloBAC11 (Research Genetics) is derived from the endogenous E. coli F plasmid. The F backbone contains four essential regions that play a role in plasmid stability and copy number. Both parA and B are required for partitioning and plasmid stability functions, parB is also required for incompatibility with regard to other F factors. OriS is the origin of F plasmid DNA replication, which is unidirectional. repE encodes protein E, essential for replication from OriS and for copy number control. A chloramphenicol resistance gene was incorporated for antibiotic selection of transformants. pBeloBAC11 encodes the lacZ gene, and thus the identification of recombinant DNA clones is simplified by blue/white selection. The most widely used E. coli strain for BAC cloning is DH10B (Grant et al. 1990. PNAS 87:4645). Key features of this strain include mutations that block: 1) restriction of foreign DNA by endogenous restriction endonucleases (hsdRMS); 2) restriction of DNA containing methylated DNA (5' methyl cytosine or methyl adenine residues,and 5' hydroxymethyl cytosine) (mcrA, mcrB, mcrC, and mrr); 3) recombination(recA1).

BAC plasmids are most popularly used for genome mapping, positional cloning, and DNA sequencing. One can also analyze expression of heterologous activities encoded by a BAC insert. Whereas the single copy nature of BAC vectors contributes to insertion stability, this same property is usually a liability for purifying and sequencing BAC DNA. A large volume of culture is needed to obtain enough plasmid DNA for conventional uses. The large volume introduces significant chromosomal DNA contamination of plasmid preparations, which often interferes with subsequent manipulations of the vector, including DNA sequencing reactions. To minimize co-purification of chromosomal DNA, conventional DNA isolation protocols must be considerably modified and therefore are not easily amenable to high-throughput protocols for plasmid DNA isolation and sequencing.

An additional potential liability of the single copy BAC vector relates to expression of heterologous DNA in E. coli. Expression can be limited by single plasmid copy number, especially if expression is reliant on foreign promoters present in the heterologous insert.

Our invention provides methods that facilitate 1)cloning of large inserts into BAC plasmids 2) isolation of large amounts of BAC DNA (by increasing plasmid copy number), and 3) increasing heterologous expression from BAC plasmid inserts (by increasing plasmid copy number and/or introducing promoters into the insert).

SUMMARY OF THE INVENTION

Cloning and sequencing of large DNA fragments has become increasingly necessary as more researchers enter the field of genomics. Although many vectors and tools are available for these tasks, such vectors are often low copy so that the large DNA inserts are stably maintained within the vector. A major impediment to the use of low copy number vectors is the difficulty in preparing large quantities of vector for cloning and sequencing. In particular, automated sequencing techniques are not adapted for use with low copy vectors. Expression of gene products encoded by large DNA inserts may also suffer due to the low copy number of the vectors. The invention described herein provides novel vectors for improving cloning, sequencing and expression of DNA inserts in low copy vectors. In one aspect, the invention provides a vector for increasing the copy number of plasmids, comprising a transposable element containing a moderate or high copy number origin of replication capable of in vitro transposition into a target plasmid. The target plasmid is a single or low copy plasmid, e.g. a BAC vector, that is useful for cloning large pieces of DNA. The transposon plasmid may contain any moderate or high copy origin of replication that is compatible with a bacterial host such as E. coli. Thus, an exemplary ori is the colE1 ori from pBR322. Expression of gene products encoded by the DNA inserts is facilitated by addition of a transcription control sequence to the transposable element. In certain embodiments, the transcription control sequence is the T7 promoter, which is functional in cells expressing the T7 RNA polymerase. Other promoters that are useful for increasing expression of cloned genes include endogenous bacterial promoters.

The vectors may further comprise one or more antibiotic resistance genes, such as those for ampicillin, tetracycline or kanamycin. In addition, they may contain a counterselectable marker, such as the sacB gene from B. subtilis, to insure that only transformants which take up the target plasmid will survive.

The vector components described above may be combined in a number of ways to provide novel vectors. For example, one such vector may comprise (a) a transposable element containing a high copy number origin of replication, (b) an antibiotic resistance gene and (c) a counterselectable marker. Other vectors may contain a transcription control sequence in addition to the above components. One exemplary vector is pTRANS-sacB, which contains (a) a transposable element containing a pBR322 origin of replication, (b) a kanamycin resistance gene, (c) a B. subtilis sacB gene, and (d) a T7 promoter.

Another possible combination of components is found in a vector comprising (a) a transposable element containing a high copy number origin of replication, (b) an antibiotic resistance gene, and (c) a transcription control sequence. An exemplary vector of this type is pTRANS, which contains (a) a transposable element containing a pBR322 origin of replication, (b) a kanamycin resistance gene, and (c) a T7 promoter.

The invention also provides methods for using such transposon plasmids.

For example, the invention provides a method for increasing the copy number of a target plasmid comprising: mixing, in vitro, the target plasmid with any of the vectors described above under conditions permitting introduction of the high copy number origin of replication into the target plasmid.

As mentioned, sequencing from BAC and other low copy vectors is difficult due to the necessity of using large numbers of cells to obtain sufficient DNA for sequencing. The invention thus provides a method for sequencing a gene in a low copy number plasmid, comprising mixing, in vitro, the target plasmid with transposon vector of this invention, transforming the mixture and determining the sequence of genes isolated from selected transformants. Transformants which have the transposon introduced into a useful locus in the target plasmid may be screened for by detecting a phenotypic change in the clones transformed with the mixture relative to clones transformed with BAC vector alone. Phenotypic changes that may be observed include an increase or decrease in gene expression.

Vectors containing transcription control sequences may be used to increase expression of a gene in a target plasmid by mixing such vectors in vitro with a target plasmid and then transforming the mixture into cells capable of recognizing the transcription control element and expressing the gene. For example, a target plasmid into which a transposon containing a T7 promoter has been introduced may be transformed into cells expressing T7 polymerase.

The plasmids of this invention also facilitate full length cloning of genes, e.g. those isolated from a plurality of organisms or from a genomic source. The method for full length cloning of genes comprises mixing a BAC library with a transposon plasmid of this invention to increase the copy number of the plasmids, and then isolating large amounts of DNA and cloning full length genes.

Another use for these plasmids is to generate shuttle vectors without cloning. The invention provides a method for generating a shuttle vector comprising mixing, in vitro, a target plasmid with a vector comprising a transposable element containing an origin of replication for a host different from that of the target plasmid, under conditions permitting transposition of the ori into the target plasmid. If desired, the ori may be a moderate or high copy number ori.

In another aspect, the invention provides improved BAC vectors which facilitate cloning of large DNA fragments into low copy vectors. These improved BAC vectors comprise a high copy origin of replication flanked by cleavage sites for a restriction enzyme, wherein cleavage of the vector with the restriction enzyme leaves single base extensions for cloning and removes the high copy origin of replication. In some embodiments, the vectors further comprise a BST X1 site. An exemplary vector of this type is pBacTA.PUC2.

BRIEF DESCRIPTION OF THE FIGURES

FIG. 8. pBTP2—A further iteration of this vector removes an EcoRI site outside the polylinker and adds EcoRI to the polylinker. See SEQ ID NO. 9, before, and SEQ ID NO. 10, after.

FIG. 10. Illustration of random insertion of promoters into metagenomic library using a modified tn5 transposon. The boxed figure at the bottom represents the optimum insertion pattern.

DETAILED DESCRIPTION OF THE INVENTION

Definitions

Figure 1:
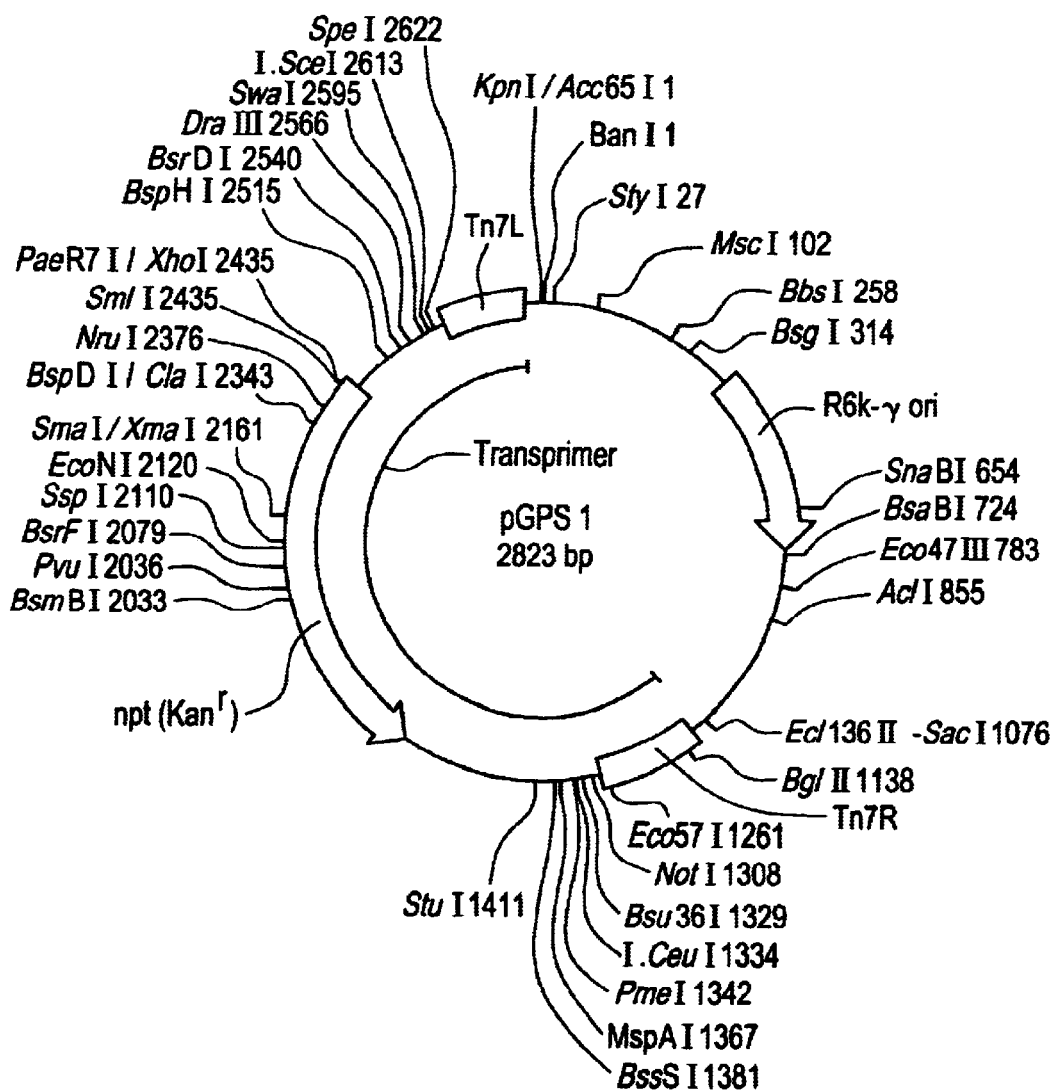
FIG. 1. Plasmid pGPS1. Commercially available transposon plasmid from New England Biolabs.

For convenience, the intended meaning of certain terms and phrases used herein are provided below:

An "antibiotic resistance gene" is a gene which encodes a protein that confers on a cell resistance to one or more specific antibiotics.

A "coding sequence" or a sequence which "encodes" a particular polypeptide or RNA, is a nucleic acid sequence which is transcribed (in the case of DNA) and translated (in the case of mRNA) into a polypeptide in vitro or in vivo when placed under the control of an appropriate expression control sequence. The boundaries of the coding sequence are generally determined by a start codon at the 5' (amino) terminus and a translation stop codon at the 3' (carboxy)

terminus. A coding sequence can include, but is not limited to, cDNA from proaryotic or eukaryotic mRNA, genomic DNA sequences from procaryotic or eukaryotic DNA, and synthetic DNA sequences. A transcription termination sequence will usually be located 3' to the coding sequence.

A "construct", e.g., a "nucleic acid construct" or "DNA construct", refers to a nucleic acid or nucleic acid sequence.

"Copy number" refers to the number of copies of a vector present in a cell, which is determined by its origin of replication. A vector with a low copy number exists in less than five copies in the cell, most often in only a single copy. Moderate copy number vectors, such as those with a pBR322 ori, exist in about 20–40 copies per cell, usually about 30 copies. High copy number vectors, e.g., pUC based vectors, exist in about 100 or more copies per cell.

A "counterselectable marker" is a gene or genes encoding a property that is lethal or inhibitory to cell growth. Lethality or growth inhibition may result, e.g., from 1) induction of expression of the gene or genes, 2) constitutive expression of a gene(s) which is toxic under certain growth conditions, 3) growth in the presence of a toxic drug or chemical (in the absence of a resistance gene). Examples of counterselectable markers are: sacB gene, inhibits growth of E. coli in the presence of 5% sucrose; phage lysis genes, expression of phage lysis genes (such as lambda phage lysis genes) kills E. coli; F-plasmid ccdB gene, expression of ccdB gene kills E. coli by inhibiting DNA gyrase; colicin release genes (such as the kit gene for colicin E1), expression of kil gene kills E. coli.

"Gene" refers to a nucleic acid molecule or sequence comprising an open reading frame and including at least one exon and (optionally) one or more intron sequences.

"Nucleic acid" refers to polynucleotides such as deoxyribonucleic acid (DNA), and, where appropriate, ribonucleic add (RNA). The tern should also be understood to include derivatives, variants and analogs of either RNA or DNA made from nucleotide analogs, and, as applicable to the embodiment being described, single (sense or antisense) and double-stranded polynucleotides.

"origin of replication" or "ori" is a sequence of DNA at which replication is initiated.

A "shuttle vector" is a vector that is able to replicate in more than one type of host cell. Typical shuttle vectors contain two origins of replication.

A "target plasmid", as the term is used herein, refers to a low copy plasmid, such as a BAC vector, which is the recipient of the transposable element and which may replicate at high copy with the introduction of the high copy ori.

"Transcription control sequence" refers to DNA sequences, such as initiation signals, enhancers, promoters and silencers, which induce or control transcription of DNA sequences with which they are operably linked. Control elements of a gene may be located in introns, exons, coding regions, and 3' flanking sequences. Some control elements are "tissue specific", i.e., affect expression of the selected DNA sequence preferentially in specific cells (e.g., cells of a specific tissue), while others are active in many or most cell types. Gene expression occurs preferentially in a specific cell if expression in this cell type is observably higher than expression in other cell types. Control elements include so-called "leaky" promoters, which regulate expression of a selected DNA primarily in one tissue, but cause expression in other tissues as well. Furthermore, a control element can act constitutively or inducibly. An inducible promoter, for example, is demonstrably more active in response to a stimulus than in the absence of that stimulus. A stimulus can comprise a hormone, cytokine, heavy metal, phorbol ester, cyclic AMP (cAMP), retinoic acid or derivative thereof, etc.

"Transposable element" or "transposon" refers to a DNA sequence able to move or "hop" from its original location and insert itself into a new location within new DNA sequence. The new site of insertion is a base sequence with which the element has no homology. Hopping (transposition) is not dependent on bacterial recombination functions.

The term "vector" refers to a nucleic acid molecule capable of transporting another nucleic acid to which it has been linked. One type of vector is an episome, i.e., a nucleic acid capable of extrachromosomal replication. Often vectors are used which are capable of autonomous replication and/or expression of nucleic acids to which they are linked. Vectors capable of directing the expression of an included gene operatively linked to an expression control sequence can be referred to as "expression vectors". Expression vectors are typically in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of vectors which serve equivalent functions and which are or become known in the art.

Plasmids Encoding a Moderate or High Copy Origin of Replication Transpos n

The plasmids of this invention facilitate use of BAC vectors and other low copy number vectors useful for research in which large cDNA or genomic inserts must be cloned into vectors. For example, in genomics research, large fragments of the gerome are cloned into vectors for sequencing or expression. Low copy vectors which can be used as target plasmids for the purposes of this invention are those vectors which contain very low copy oris (1–2 copies/cell), such as bacteriophage P1, F plasmid and R1 plasmid, or low copy oris, such as plasmid pSC101 (about 5 copies per cell), plasmid p15A (10–12 copies per cell) or plasmid RK2 (4–7 copies per cell.)

One object of the invention is to provide a vector comprising a transposable element which is capable of random in vitro transposition into a target plasmid. The plasmids of this invention contain a moderate or high copy number origin of replication (hereafter referred to as an ori) within the transposable sequence. Transposon plasmids are known in the art. Such plasmids have been used to facilitate sequencing reactions by "hopping" into random sites in a target plasmid. Since the transposon ends can be used to prime sequencing reactions, the number of primers required for sequencing is reduced, and the necessity of sequencing overlapping ends in order to generate new sets of primers is eliminated. Using transposon vectors, one can sequence large numbers of clones simultaneously using a single set of primers. However, commercial transposon plasmids used for sequencing generally contain a defective origin of replication which cannot replicate in wild type bacterial cells, whereas the plasmid of this invention contain a high copy origin of replication within the transposable sequence. The transposition of the high copy ori into the target plasmid allows the target plasmid to replicate to high copy number within the host cell. Other plasmids are known which contain transposable oris which are useful in certain applications involving in vivo cloning. In those cases, the transposon hops into the chromosome, bringing with it the high copy ori. The gene and high copy ori are either excised with restriction enzymes or packaged into phage. Recircularization of the excised or packaged piece is then required to provide a plasmid which can replicate in high copy. Additionally, if the practitioner then desired to sequence genes cloned with these transposon plasmids, the genes would need to be subcloned into a sequencing vector. In contrast, the plasmids of this invention can transpose in vitro into a low copy number vector to insert a moderate or high copy ori. This improvement is particularly significant in a number of very important applications, such as are described below. Using these plasmids, a second recircularization step is not necessary: insertion of the transposon alone provides the target plasmid with the ability to replicate at high copy number permitting sequencing without the need for additional subcloning.

Components of the Vectors

Origins of replication to be used in the plasmids of this invention may be moderate copy, such as the colE1 ori from pBR322 (15–20 copies per cell) or the R6K plasmid (15–20 copies per cell), or may be high copy, e.g. pUC oris (500–700 copies per cell), pGEM oris (300–400 copies per cell) pTZ oris (>1000 copies per cell) or pBluescript oris (300–500 copies per cell). The origins of replication in the transposon may be functional in *E. coli* or in any other prokaryotic cell type, such as Bacilli (e.g., *B. subtilis*) or Streptomycetes.

The plasmids may further contain an antibiotic resistance gene within the transposable sequence, for selection on antibiotic-containing plates. Commonly used antibiotic resistance genes are genes for resistance to ampicillin, kanamycin, tetracycline, chloramphenicol, etc. The plasmid may contain any one or more of such antibiotic resistance genes.

Additionally, the plasmids may contain one or more transaction control sequences. One such sequence should be found within the transposable sequence, such that when the transposon hops into the target plasmid, it carries along with it the transcription control sequence. An exemplary sequence is the T7 promoter, but any promoter or enhancer that is functional in prokaryotic cells may be used. Usefull promoters include, but are not limited to, lac (*E. coli*), trp (*E. coli*), araBAD (*E. coli*), tac, hybrid, (*E. coli*), trc, hybrid (*E. coli*), lpp-lac hybrid (*E. coli*), PL ($\lambda$), T7-lac operator and $\lambda$PL, PT7 ($\lambda$, T7).

The plasmids may also contain a counterselectable marker, which is outside of the transposable sequence. The presence of a counterselection marker ensures that any transformant that has received the original transposon plasmid will be selected against, since the counterselectable marker causes lethality in the host cell. For example, the counterselectable marker can be the sacB gene from *B. subtilis*. When cells expressing sacB are grown on sucrose containing medium, sucrose polymers are formed which are toxic to the cells. Other counterselectable markers useful in this invention are phage lysis genes (such as lambda phage lysis genes), the F-plasmid ccdB gene (works by inhibiting DNA gyrase) and colicin release genes (such as the kil gene for colicin E1).

Figure 2:
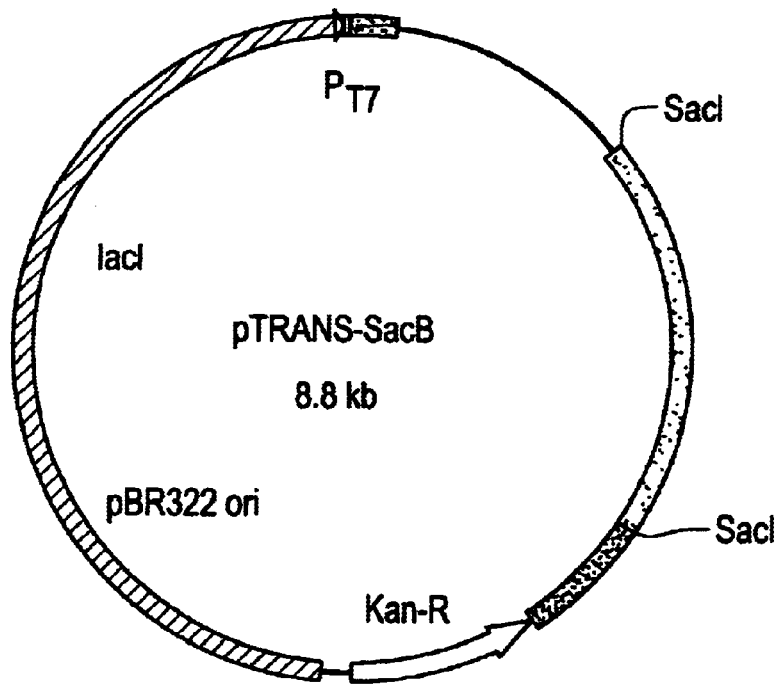
FIG. 2. Plasmid pTRANS-SacB. The transposable region contains sequences encoding a T7 promoter, a lad gene, a pBR322 origin of replication and a kanamycin resistance gene. Plasmid pTRANS-SacB also encodes a counter-selectable marker, the *B. subtilis* sacB gene, located outside of the transposable region. Expression of sacB, encoding the enzyme levansucrase, is lethal to *E. coli* in the presence of 5% sucrose. $P_{T7}$, T7 promoter; lac l, lac repressor gene; pBR322 ori, origin of replication from plasmid pBR322; SacB, *B. subtilis* sacB gene.

In a preferred embodiment, the transposon plasmid is pTRANS-sacB (FIG. 2). A commercially available transposon plasmid, pGPS1, (New England Biolabs, FIG. 1) was used as a starting point In the construction of pTRANS-sacB. pGPS1 contains a defective origin of replication which is non-functional in wild-type *E. coli*. It also contains universal primer sites for DNA sequencing at both ends of the transposable element. Several modifications have been made to pGPS1 to generate pTRANS-sacB. A moderate copy origin of replication (the pBR322 ori) has been introduced into the transposon ("trans"). Universal primer sites for DNA sequencing (from pGPS1) are encoded at both ends of trans and a T7 promoter, directed "outward" (i.e., away from the transposable element), is encoded on one end. The plasmid also contains the *B. subtilis* sacB gene for counterselection. In vitro transposition of trans into a single copy BAC vector introduces a moderate copy ori, thereby increasing the copy number of the target BAC vector.

Uses for Vectors Containing Transposable Elements

1) Transposon Mutagenesis With pTRANS-sacB Increases BAC Vector Copy Number and Facilitates Automated DNA Isolation and Sequencing.

a) General use for Sequencing BAC Inserts.

Isolation of low-copy plasmids for DNA sequencing requires plasmid purification from large numbers of *E. coli* cells. As a result, the DNA is frequently "dirty", i.e. contaminated with fragmented chromosomal DNA which can interfere with subsequent DNA sequencing reactions. Since low-copy plasmid DNA isolation protocols require careful technical manipulation, these protocols are not amenable to automated "high-throughput" methods normally used for high-copy plasmids. Transposition of a high copy origin of replication into specific BAC plasmids of interest increases the BAC copy number. Thus, fewer cells are required to obtain the amount of DNA needed, thereby facilitating automated DNA isolation and sequencing.

Transposition of trans into a single copy BAC plasmid has been shown to increase copy number, facilitating plasmid isolation. pTRANS-SacB has successfully been used to sequence large soil BAC plasmids containing greater than >30 kb DNA using automated DNA isolation and sequencing methods. Automated plasmid isolation and automated sequencing is not possible with single copy plasmids, therefore plasmids of this invention such as pTRANS-SacB are valuable tools for automated DNA sequencing of single or low copy plasmids containing large inserts.

b) Sequencing of a Particular Gene Contained in a Large BAC Insert. One can "knock-out" a particular activity encoded on a low-copy BAC plasmid with the transposon plasmids of this invention. Knockout occurs when the transposable element inserts itself into the coding region of a gene contained within the BAC vector. Such transpositions physically link the transposable element to the DNA encoding that activity and simultaneously increase the plasmid copy number for automated DNA isolation and sequencing.

2) Plasmid pTRANS-sacB as a Tool for Increasing Heterologous Gene Expression From a Given BAC Plasmid or a Pooled BAC Library.

a) Increasing Expression Through Increasing Plasmid Copy Number. Increasing the copy number of a given BAC plasmid or a BAC library is one way to increase heterologous gene expression and may allow for detection of new activities previously too low to detect from single copy plasmids. Subjecting either a given BAC clone or a pooled BAC library to transposon mutagenesis using the transposon plasmids described herein will increase the copy number of the BAC plasmids. In the case of a pooled BAC library, the resulting DNA library, containing random trans insertions can then be transformed into *E. coli* and the resulting transformants screened for new activities.

Transposition of trans into a given BAC plasmid has been shown to increase heterologous expression from that BAC plasmid. We have demonstrated increased heterologous expression, resulting from increased copy number, from plasmids encoding antibacterial activities, lipase activities and pigment. Increased expression of heterologous activities allows one to overproduce the activity, greatly facilitating biochemical analysis of the activity.

In one embodiment, the library contains DNA inserts from a plurality of organisms. For example, transposition of trans into a BAC library of DNA isolated from soil, followed by transformation into E. coli, essentially generates a new library with increased copy number, potentially permitting detection of new activities not previously detectable from the low copy version of the library. This procedure allows one to first done a large insert library in a more stable, low copy vector, and then increase the copy number when it is desirable.

Transposition of trans into a given clone encoding a biosynthetic gene cluster may disrupt that gene cluster in such a way as to produce a new biological activity. Since biosynthesis of natural products such as polyketides is a stepwise enzymatic process, disruption of a gene encoding an intermediate step permits accumulation of a biosynthetic intermediate which may have a novel biological activity (that one may never otherwise have seen had the duster remained intact). Increased copy number may permit overproduction of this activity, facilitating its detection, as described in Examples 4 and 5.

b) Increasing Expression Through Promoter Insertion

Figure 5:
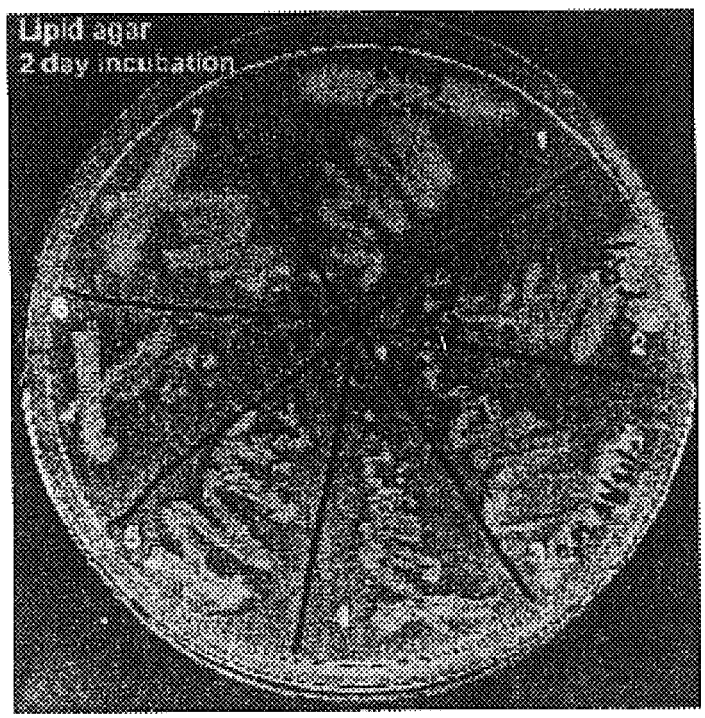
FIG. 5. Amplification of lipase expression from a BAC clone by increasing copy number with pTRANS-SacB.

As described above, the transposon directed insertion of high copy origins of replication can modify plasmid copy number, host utilization and level of production of molecules encoded within the foreign DNA inserts. However, transcription and expression of genes from other organisms phylogenetically distant from the E. coli host strain may be below the level of detection in subsequent screens. In addition, many natural products are encoded in multi-gene clusters with promoters running in both directions (see FIG. 5). A further application of this system utilizes a second transposon based system for the random introduction of multiple bacterial promoters which function in E. coli. The transposon system described above is based on Tn-7 bacterial transposon. This system has a characteristic termed "target immunity" which inhibits more than one transposable element within a 190 kb contiguous strand of DNA (Anne E. Stellwagen and Nancy L. Craig *Avoiding self: two Tn7-encoded proteins mediate target immunity in Tn7 transposition*. EMBO J. 1997 16: 6823–6834.). Conversely, a transposon system based on Tn-5 has no such immunity system (Igor Yu Goryshin and William S. Reznikoff Tn5 in Vitro Transposition J. Biol. Chem. 1998 273: 7367–7374). Constructing a transposon based on this system and incorporating a strong bi-directional bacterial promoter (with or without a selectable marker) allows for the introduction of multiple transposons at random sites within a BAC library of DNA isolated from soil. By controlling the transposon/target ratio, one may obtain a defined range of transposon insertions per single plasmid insert. A variation on this is to add a reporter gene such as GFP within the transposon and select bacteria (based on fluorescence) to obtain an optimum number of insertions where every additional GFP gene would cause an incremental increase in fluorescence detectable by standard flow cytometry. Many of the insertions will disrupt transcription, however the transposition is done multiple times on one library to obtain a large pool of randomly inserted promoters.

3) Facilitation of Full-length Genomic Cloning Using pTRANS:

Since BAC vectors stably accommodate large DNA inserts, they are often the vector of choice for genomic cloning. However, their low copy number often makes it difficult to isolate full length clones, since large numbers of cells would be required to provide a sufficient amount of DNA for cloning. Use of a vector which increases copy number, e.g. pTRANS, can facilitate full-length cloning by allowing library construction in a BAC vector. Once the library is obtained, the copy number can be increased by using pTRANS or a similar vector, enabling cloning of full-length, large pieces of genomic DNA.

4) Construction of Shuttle Vectors:

The plasmids of this invention allow expedited construction of shuttle vectors without the need for cloning. In order to constrict a shuttle vector using transposon plasmids, the transposon plasmid should contain an ori for expression in a host other than the host in which the target plasmid can replicate. For example, the transposon may contain a *B. subtilis* ori, while the target plasmid contains an *E. coli* ori. Following the in vitro transposition reaction, the resultant vector is able to replicate in both *B. subtilis* and *E. coli*.

Improved BAC Vectors

Although BAC vectors are widely used for cloning large DNA fragments (>25 kb), it remains difficult to done such large inserts. The improved BAC vectors of this invention contain modifications to traditional BAC vectors that improve cloning and make the vectors an increasingly useful tool in genomics research. Specifically, the cloning vectors of this invention contain a high copy ori to facilitate large scale preparation of vector. The high copy ori is flanked by restriction sites, such that cloning of insert into the vector removes the high copy ori, restoring the vector to its original low copy number and improving stability of large DNA inserts. Additionally, cleavage of the vector with the restriction enzyme that removes the high copy ori leaves single base extensions on the vector. These extensions facilitate cloning of large fragments of genomic DNA. Other modifications include the addition of BST X1 sites. The presence of this site allows the practitioner to increase the length of overhang on a genomic fragment by addition of BST X1 linkers. Generally, fragments of DNA with longer overhangs are easier to done than those with single base extensions.

Exemplary cloning vectors utilize plasmids which are based on the *E. coil* F-factor replicon. The F-factor replicon allows for strict copy number control of the clones so that they are stably maintained at 1–2 copies per cell. The stability of the cloned DNA during propagation in an *E. coli* host is substantially higher in lower copy number vectors than in multi-copy counterparts (Kim et al, NAR, 20(5):1083–1085). The stabilizing effect of BAC vectors is notable especially for certain genomic DNA that are normally unstable in high copy number vectors. This includes genomes of Archaeal, mammalian, or other origins.

The pBeloBAC11 vector (a commercially available plasmid) allows lacZ-based positive color selection of the BAC clones that have insert DNA in the cloning sites at the time of library construction. There are several significant drawbacks to this vector. First, because the vector exists in single copy in *E. coli*, purifying the DNA in large quantity takes some effort. In addition, the available cloning sites are minimal and alternate cloning strategies are not possible.

Thus, improved BAC vectors of this invention are exemplified by the vector pBacTA.pUC2, which contains several significant modifications to pBeloBAC11: 1) a high copy pUC origin of replication is added to the vector to allow large scale vector purification in *E. coli*; 2) a restriction enzyme site flanks the pUC ori so that large inserts cloned into this site remove the high copy ori and allow the large DNA fragments to be stably inserted in a low copy vector 3) additional cloning sites have been introduced 4) single base extensions have been added to facilitate cloning.

The full contents of all references cited in this document, including references from the scientific literature, issued patents and published patent applications, are hereby expressly incorporated by reference.

The following examples contain important additional information, exemplification and guidance which can be adapted to the practice of this invention in its various embodiments and the equivalents thereof. The examples are offered by way of illustration only and should not be construed as limiting in any way. As noted throughout this document, the invention is broadly applicable and permits a wide range of design choices by the practitioner.

The practice of this invention will employ, unless otherwise indicated, conventional techniques of cell biology, cell culture, molecular biology, transgenic biology, microbiology, recombinant DNA, immunology, virology, pharmacology, chemistry, and pharmaceutical formulation and administration which are within the skill of the art. Such techniques are explained fully in the literature. See, for example, Molecular Cloning A Laboratory Manual, 2nd Ed., ed. by Sambrook. Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. : 4,683,195; Nucleic Acid Hybrdization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Construction of pTRANS Vectors

Figure 3:
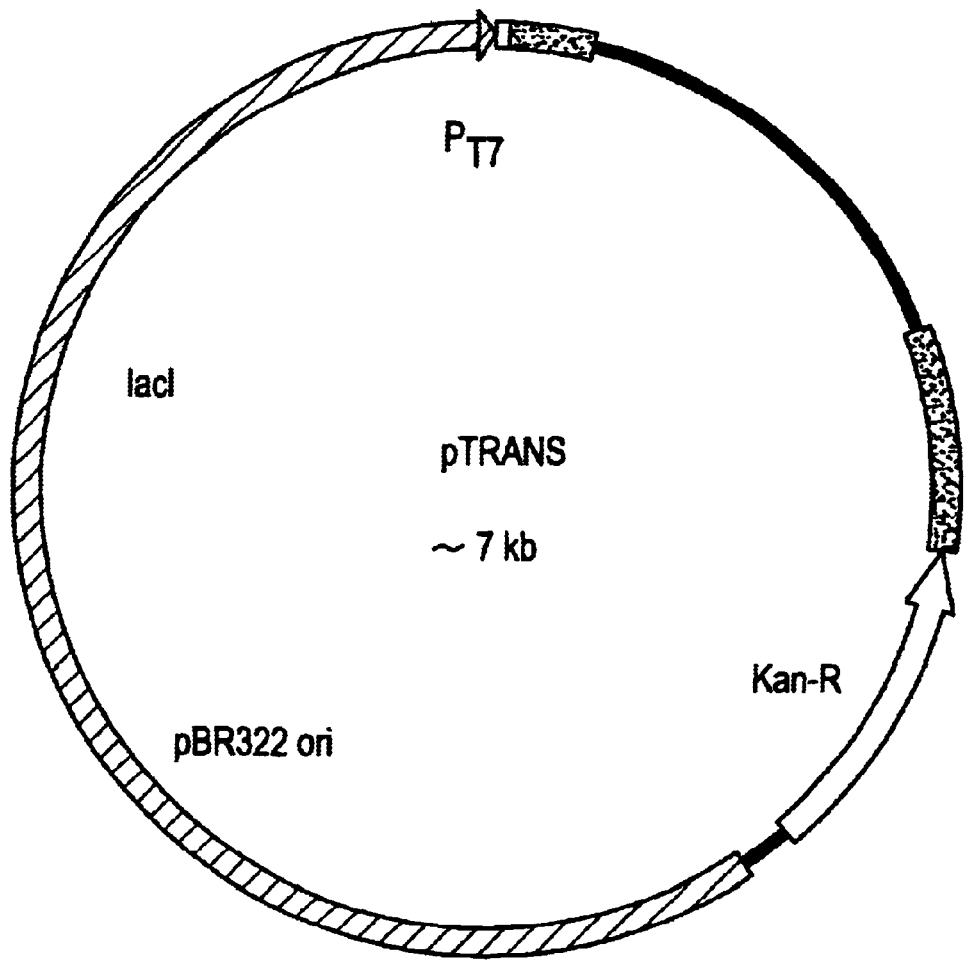
FIG. 3. Plasmid pTRANS. The transposable region contains sequences encoding a T7 promoter, a lacI gene, a pBR322 origin of replication and a kanamycin resistance gene. Plasmid pTRANS is identical to pTRANs-SacB except for the absence of the counter-selectable marker, the *B. subtilis* sacB gene. $P_{T7}$, T7 promoter, lacl, lac repressor gene; pBR322 ori, origin of replication from plasmid pBR322; SacB *B. subtilis* sacs gene.

Plasmid pTRANS-sacB. The 4.2 kb ScaI/XbaI fragment from pET-22b was cloned into plasmid pGPS1 linearized with SpeI and SwaI. The resulting kanamycin-resistant plasmid, pTRANS (FIG. 3), encodes the trans transposon, containing the high copy ori and T7 promoter from pET-22b. A 1.7 kb sacB gene, amplified from the *B. subtilis* 168 chromosome by PCR, was cloned into the unique SacI site in pTRANS. The resulting plasmid. pTRANS-sacB (FIG. 2), can be counterselected in the presence of 5% sucrose. In an in vitro transposition reaction, pTRANS-sacB and the target BAC plasmid would be mixed with transposase according to the New England Biolabs protocol, following the transposition reaction, the resulting DNA would be transformed into *E. coli* DH10B and plated on media containing kanamycin (to select for transpositions), chloramphenicol (to select for the BAC plasmid) and 5% sucrose (to counterselect pTRANS-sacB, which is lethal in the presence of sucrose). The resulting kanamycin/chloramphenicol/sucrose-resistant plasmids should be BAC plasmids containing trans.

Strain DH10B(DE3). Strain DH10B(DE3) was constructed using the DE3 lysogen kit from Novagen. Strain DH10B(DE3) expresses T7 RNA polymerase encoded by a chromosomal lysogen and is an expression host for plasmids driving heterologous expression from a T7 promoter.

Example 2

Construction of BAC Vectors

Figure 7:
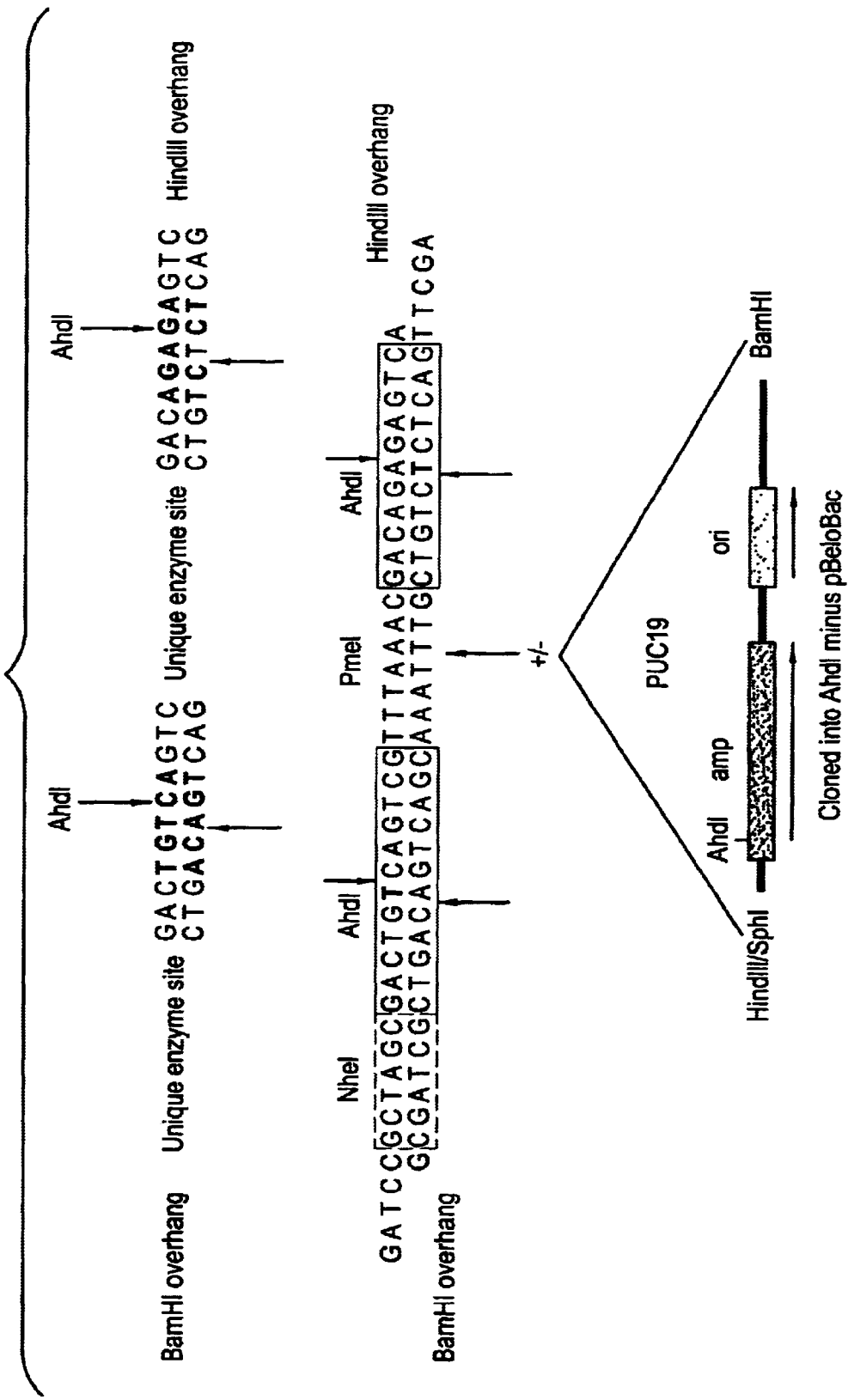
FIG. 7. BACTAPUC1 (pBTPH1)—Diagram of modified pBeloBAC11. The original vector was altered by including a modified polylinker region (SEQ ID NOs. 7 and 8) into which a high-copy PUC vector was inserted. In addition, by using a unique oligonecleotide adaptor, we have introduced the ability to utilize cloning based on single base extensions. See the AhdI sites provided by SEQ ID NOs. 3–6.

1. BACTAPUC1 (pBTP1)—The first version of the vector, pBTP1, combines pBeloBAC with a high copy PUC-based vector. As shown in FIG. 7, insertion of an entire PUC plasmid into the cloning site accomplishes several things. First, it simplifies the purification of the vector prior to cloning by virtue of the high copy ori within the PUC insert which drives the copy number to >100 copies/cell. Second, by using a unique oligonucleotide adapter, we have introduced additional cloning sites. This includes the ability to utilize cloning based on single base extensions. Thermostable polymerases such as Taq have a nontemplate-dependent activity which adds a single deoxyadenosine (A) to the 3' end of DNA. This single extended DNA will ligate efficiently with a vector that has corresponding deoxythymidine (T) ends. By incorporating a restriction site with internal degenerate internal bases, such as AhdI (GACNNNNNGTC (SEQ ID NO:1)), we can create a vector which, when cut with AhdI, leaves a single T on each end. By treating the genomic DNA with a series of polymerases (T4 and Klenow for blunting followed by Taq to add a single A) DNA can be directly cloned without the need for partial restriction digestion. This latter point is key since cloning by partial restriction digestion will decrease the average insert size of the library by at least half (see below).

The vector pTransSacB was deposited on Apr. 1, 2003 with the American Type Culture Collection (ATCC) at 10801 University Blvd., Manassas, Va. The deposit was in the form of the vector contained in the bacteria *Escherichia coli* K12 strain DH10B. The deposit received the designation PTA-5105 and was viable when tested by the ATCC on Apr. 15, 2003.

Figure 8A:
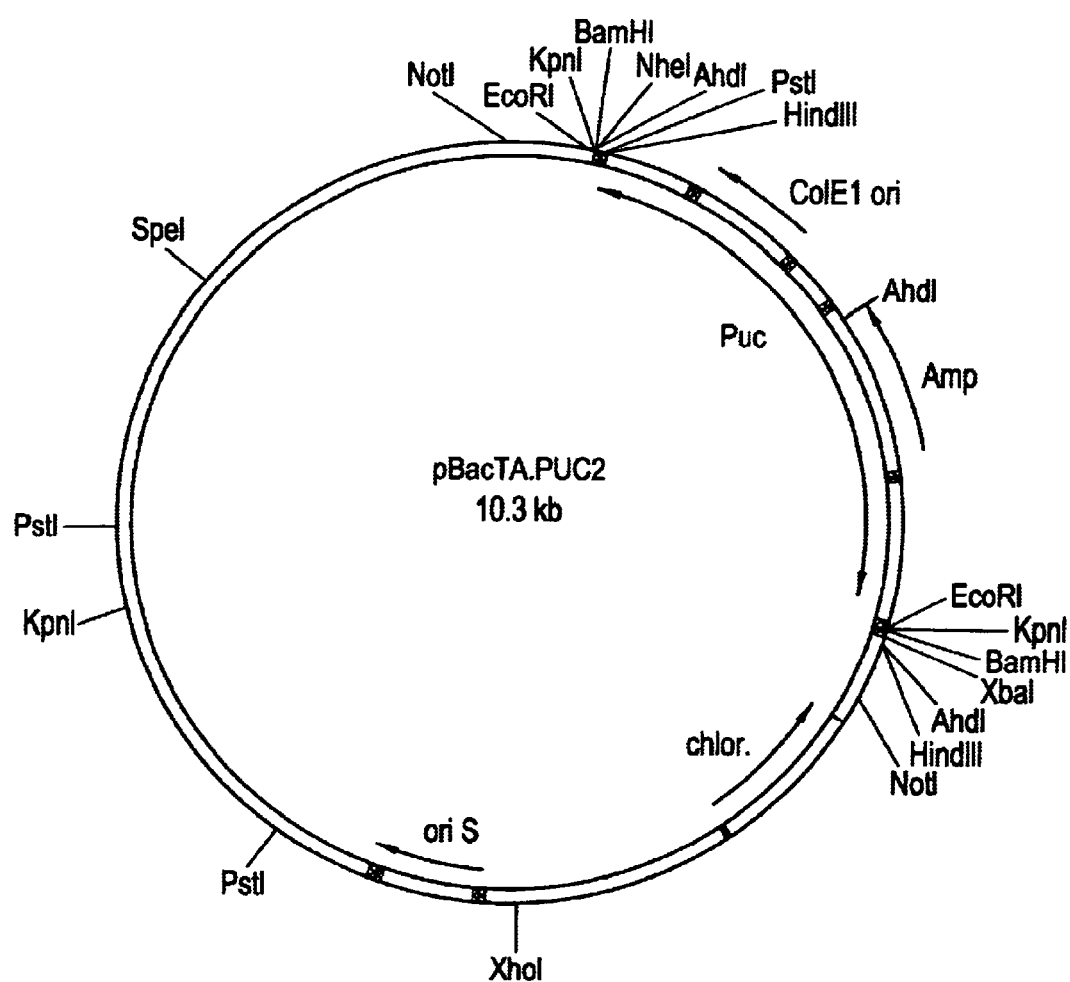
FIG. 8A. pBacTA.PUC2 (pBTP2)—A further iteration of this vector removes an EcoRI site outside the polylinker and adds EcoRI to the polylinker.
Figure 8B:
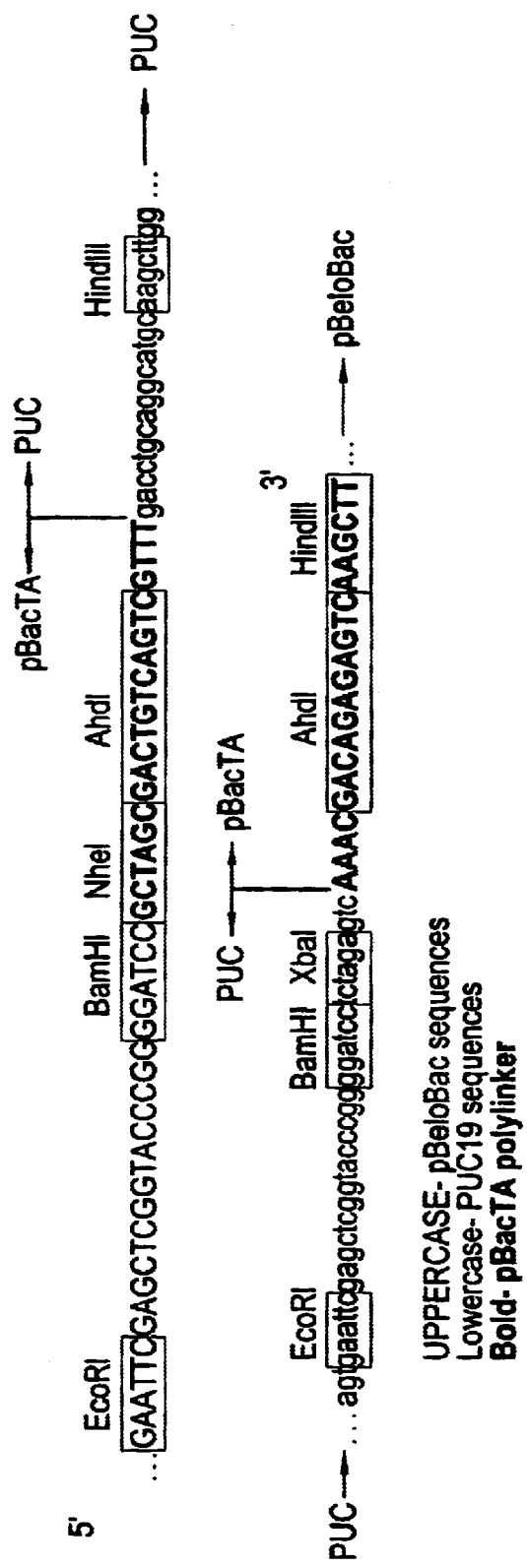
FIG. 8B. Shows changes to the vector in formation of pBTP2. SEQ ID NO. 9, on top, is the parent vector, and SEQ ID NO. 10, on bottom is pBTP2.

2. pBTP2 A further iteration of this vector (FIG. 8) removes an EcoRI site outside the polylinker and adds EcoRI to the polylinker. It is evident that in all cases, cutting the DNA with a restriction enzyme for cloning removes the PUC insert with its high copy ori and allows for the insertion of large Insert DNA into a low-copy vector.

Figure 9:
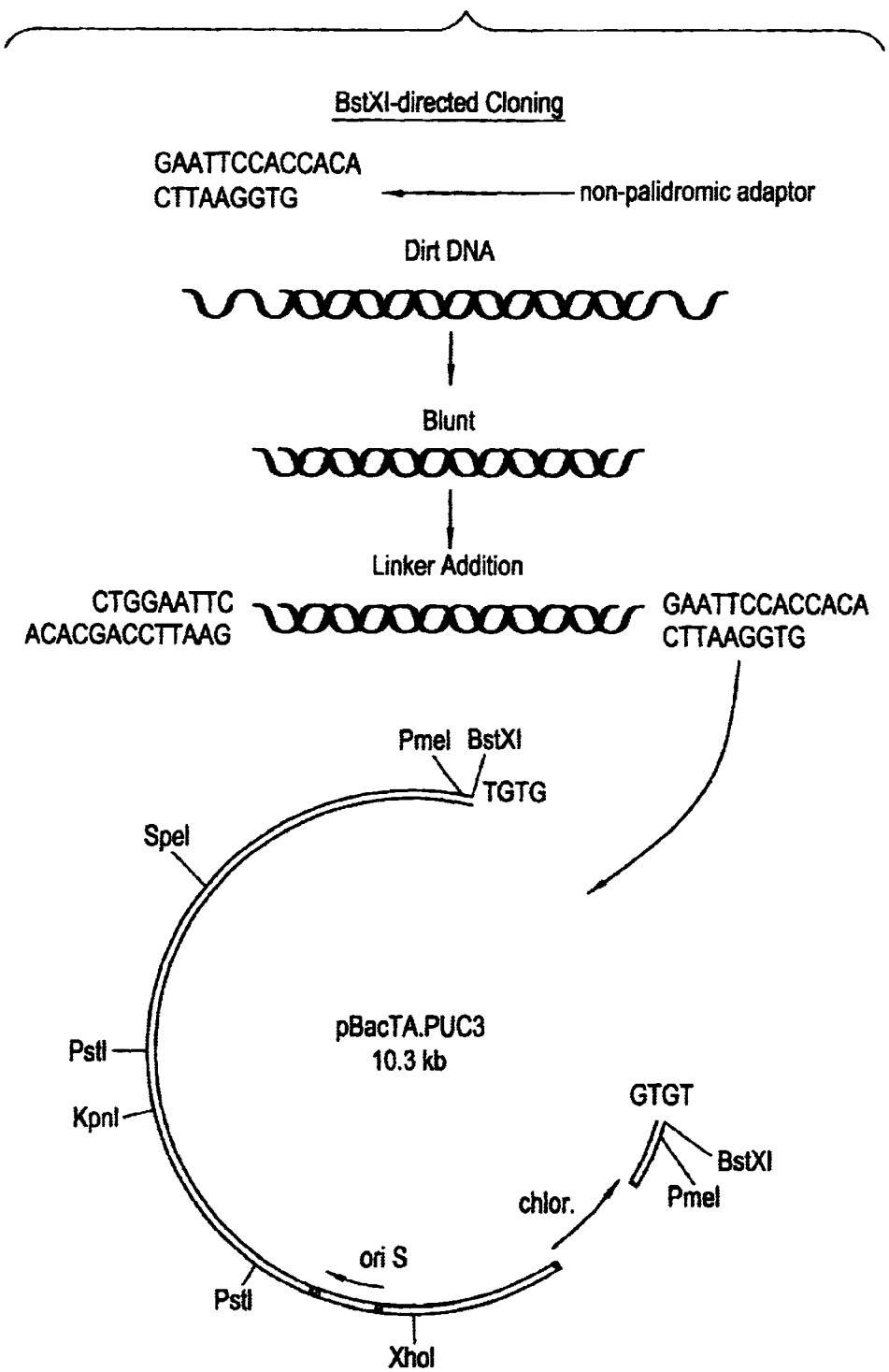
FIG. 9. pBTP3—Illustration of an adaptor system system which will allow for more efficient ligation. A BstXI restriction site is engineered into the vector such that only the appropriate modified insert (ligated with complementary adaptors, such as those shown by SEQ ID NOs. 11–14) will ligate.

3. pBTP3 As mentioned above, restriction digestion of the genomic DNA prior to cloning will decrease the average insert size of the final library. In addition, since the average size of the input DNA is in the range of 150 kb before digestion and drops to 75 kb after partial digestion, it is likely that an increasing bias will occur as we attempt to clone fragments above 80–100 kb. This will be dependent on the enzyme used for digestion and the number of sites in the DNA. Therefore, alternate strategies for cloning directly become key in constructing high quality libraries (see Table 1). The single base extension cloning system described above is one way to circumvent this problem. However, although the efficiency of cloning is greater than blunt-end cloning, it is not as high as with multiple base ligation. Also, the addition of the A tail is not 100% efficient, so not all DNA will be ligatable. An alternate approach is to incorporate non-palidromic adapters with 4-base pair overhangs which will greatly increase the efficiency of cloning. FIG. 9

(pBTP3) illustrates an example of one such system which uses a second degenerate restriction enzyme, BstXI (CCANNNNNNTGG) (SEQ ID NO:2). In this system adapters with non-homologous ends (5' CACA 3') are ligated onto blunt-end genomic DNA. These adapters will not self-ligate but will only anneal with corresponding ends which are generated in the vector by inserting the appropriate BstXI restriction site (5' GTGT 3').

TABLE 1

| | Pros | Cons |
|---|---|---|
| Restriction Digest | Compatible sticky ends, high efficiency | Need 2 sticky ends, percentage of doubly-cut DNA >100 kb is low with current dirt DNA size range, bias of library depending on enzyme used |
| Blunt Cloning | no loss in size distribution | inefficient for even small fragments, needs polishing (blunt ends) |
| Single base-pair extension cloning | no loss in size distribution, single base pair overhang increases efficiency of cloning | requires modification of ends with unknown efficiency, vector insert ratio may be critical for efficient cloning |
| Linker addition using degenerate restriction sites | no loss in size distribution, compatible sticky ends | requires polishing and linker addition with unknown efficiency |

Example 3

The Transposon Reaction

Figure 4:
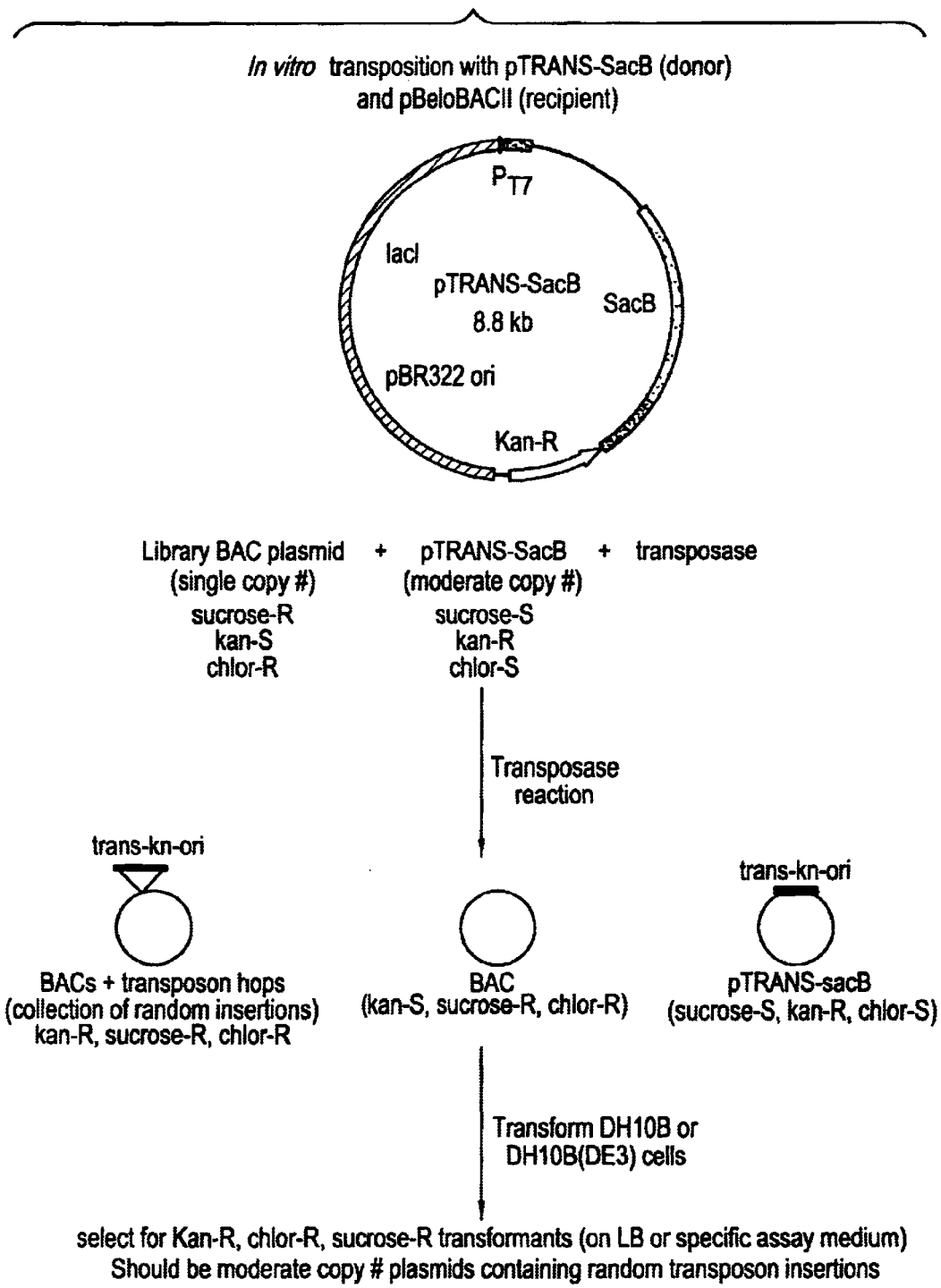
FIG. 4. Schematic of protocol for in vitro transposition reaction containing pTRANS-SacB (transposon donor) and pBeloBAC11 (recipient or target plasmid containing a DNA insert). sucrose-R, resistant to 5% sucrose; sucrose-S, sensitive to 5% sucrose; kan-R, resistant to 50 micrograms/ml kanamycin; kan-S, sensitive, to 50 micrograms/ml kanamycin; chlor-R, resistant to 10 micrograms/ml chloramphenicol; chlor-S, sensitive to 10 micrograms/ml chloramphenicol, $P_{T7}$, T7 promoter; lac l, lac repressor, pBR322 ori, origin of replication from plasmid pBR322; SacB, *B. subtilis* sacB gene.

The transposon reaction, which is shown as a schematic in FIG. 4, uses buffers and enzymes supplied in the GPS-1 Genome Priming System kit supplied by New England Biolabs. In the transposon reaction, 0.05 micrograms of pTRANS-SacB is mixed with 0.2 micrograms of a BAC target plasmid. The reaction is carried out in 1×GPS1 buffer. In a total final volume of 20 microliters. 1 microliter of TnsABC* transposase is added to the plasmid mixture, the reaction mixed and incubated for 10 minutes at 37° C. 1 microliter of start solution is then added and the reaction is mixed and incubated for 1 hour at 37° C. The transposase is inactivated by incubating the reaction at 75° C. for 10 minutes. The inactivated reaction is dialyzed against water for 1 hour. 5 microliters of reaction is transformed, by electroporation, into E. coli cells such as DH10B or DH10B (DE3). Transformants are selected on LB plates containing kanamycin (50 micrograms/ml), chloramphenicol (10 micrograms/ml), and sucrose (5%).

Example 4

Use of pTRANS to Increase Expression of Lipase From a BAC Clone

In this example, the high-copy ori was hopped into a BAC plasmid containing a lipase gene isolated from soil DNA. This activity was originally very low level, and took ~1 week of incubation to detect. A BAC plasmid, containing approximately 25 kilobases of DNA isolated from a soil sample, encoding a lipase activity, was subjected to a transposon reaction with pTRANS-SacB, as described in Example 3. The reaction was transformed by electroporation into DH10B cells and transformants were selected on LB plates containing kanamycin (50 micrograms/ml), chloramphenicol (10 micrograms/ml), sucrose (5%), and Difco lipid reagent (3%). Lipase activity was detected (as shown in FIG. 4) by a clear halo surrounding bacterial colonies, indicating digestion of lipid in the media. Several transposon hop clones expressing lipase were chosen and restreaked onto a new LB chloramphenicol lipid agar plate to directly compare several high copy lipase overproducers (clones #3,4,5, 6), a lipase knockout done (#7) and the original low copy lipase-producing BAC (#2) versus a negative control (#1). With the high copy ori, the activity is readily detectable in only 2 days, demonstrating the utility of the transposon in increasing expression.

Example 5

Use of pTRANS to Increase Expression of a Purple Pigment From a BAC Clone

In this example, the high-copy ori was hopped into a BAC plasmid containing a gene for a purple pigment isolated from soil DNA. A BAC plasmid, containing approximately 25 kilobases of DNA isolated from a soil sample encoding a purple pigment, was subjected to a transposon reaction with pTRANS-SacB, as described in Example 3. The reaction was transformed, by electroporation into DH10B cells and transformants were selected on LB plates containing kanamycin (50 micrograms/ml), chloramphenicol (10 micrograms/ml) and sucrose (5%).

Figure 6:
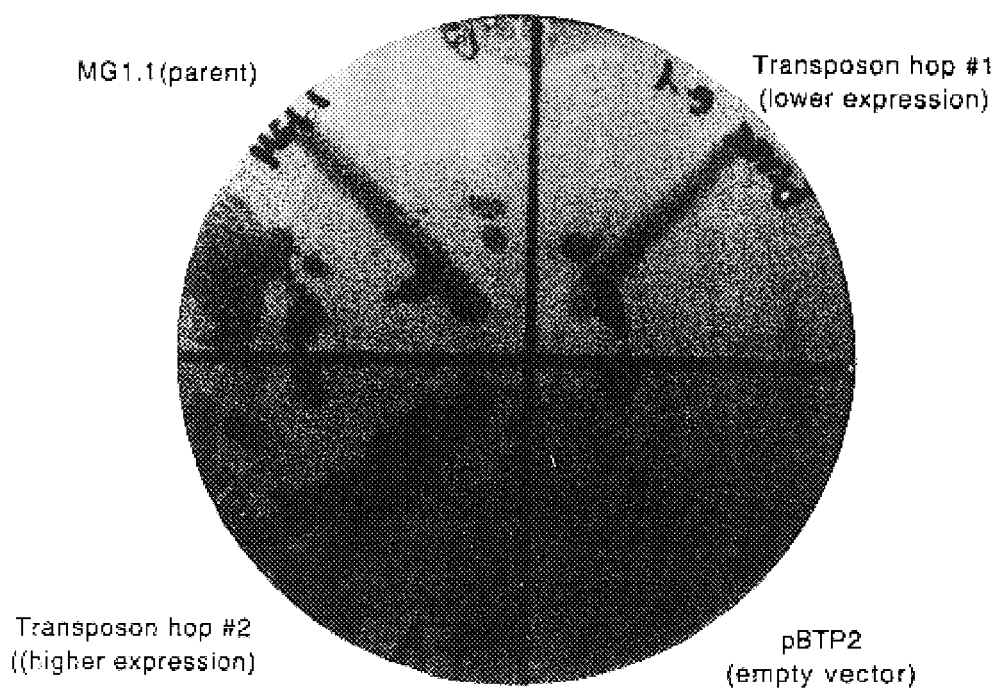
FIG. 6. Amplification of pigment expression from a BAC clone by increasing copy number with pTRANS-SacB.

FIG. 6 depicts two independent transposition events within MG1.1, a single library clone which has been shown to produce a pigmented natural product. For comparison, also represented is a non-pigmented control and the original parent. As is evident from the figure, the introduction of the high copy pTRANS can increase the production of genes within a single clone by virtue of the increase in copy number. This affects both the overall levels of the pigment as well as accelerating the rate of pigment production.

What is claimed is:
1. The vector pTRANS-SacB.
2. The vector pTRANS.
3. The vector pBacTA.PUC2.

* * * * *

SEQUENCE LISTING

<160> NUMBER OF SEQ ID NOS: 14

<210> SEQ ID NO 1
<211> LENGTH: 11
<212> TYPE: DNA
<213> ORGANISM: Artificial Sequence
<220> FEATURE:
<223> OTHER INFORMATION: Restriction enzyme site
<221> NAME/KEY: misc_feature
<223> OTHER INFORMATION: n= a or g or c or t/u

```
<400> SEQUENCE: 1
gacnnnnngt c                                                          11

<210> SEQ ID NO 2
<211> LENGTH: 12
<212> TYPE: DNA
<213> ORGANISM: Artificial Sequence
<220> FEATURE:
<223> OTHER INFORMATION: restriction enzyme site
<221> NAME/KEY: misc_feature
<223> OTHER INFORMATION: n= a or g or c or t/u

<400> SEQUENCE: 2
ccannnnnnt gg                                                         12

<210> SEQ ID NO 3
<211> LENGTH: 11
<212> TYPE: DNA
<213> ORGANISM: Artificial Sequence
<220> FEATURE:
<223> OTHER INFORMATION: Restriction enzyme site

<400> SEQUENCE: 3
gactgtcagt c                                                          11

<210> SEQ ID NO 4
<211> LENGTH: 11
<212> TYPE: DNA
<213> ORGANISM: Artificial Sequence
<220> FEATURE:
<223> OTHER INFORMATION: Restriction enzyme site

<400> SEQUENCE: 4
gactgacagt c                                                          11

<210> SEQ ID NO 5
<211> LENGTH: 11
<212> TYPE: DNA
<213> ORGANISM: Artificial Sequence
<220> FEATURE:
<223> OTHER INFORMATION: Restriction enzyme site

<400> SEQUENCE: 5
gacagagagt c                                                          11

<210> SEQ ID NO 6
<211> LENGTH: 11
<212> TYPE: DNA
<213> ORGANISM: Artificial Sequence
<220> FEATURE:
<223> OTHER INFORMATION: Restriction enzyme site

<400> SEQUENCE: 6
gactctctgt c                                                          11

<210> SEQ ID NO 7
<211> LENGTH: 42
<212> TYPE: DNA
<213> ORGANISM: Artificial Sequence
<220> FEATURE:
<223> OTHER INFORMATION: Polylinker sequence

<400> SEQUENCE: 7
gatccgctag cgactgtcag tcgtttaaac gacagagagt ca                        42
```

```
<210> SEQ ID NO 8
<211> LENGTH: 42
<212> TYPE: DNA
<213> ORGANISM: Artificial Sequence
<220> FEATURE:
<223> OTHER INFORMATION: polylinker sequence

<400> SEQUENCE: 8
agcttgactc tctgtcgttt aaacgactga cagtcgctag cg            42

<210> SEQ ID NO 9
<211> LENGTH: 71
<212> TYPE: DNA
<213> ORGANISM: Artificial Sequence
<220> FEATURE:
<223> OTHER INFORMATION: polylinker sequence

<400> SEQUENCE: 9
gaattcgagc tcggtacccg gggatccgct agcgactgtc agtcgtttga cctgcaggca   60
tgcaagcttg g                                                        71

<210> SEQ ID NO 10
<211> LENGTH: 60
<212> TYPE: DNA
<213> ORGANISM: Artificial Sequence
<220> FEATURE:
<223> OTHER INFORMATION: polylinker sequence

<400> SEQUENCE: 10
agtgaattcg agctcggtac ccggggatcc tctagagtca acgacagag agtcaagctt    60

<210> SEQ ID NO 11
<211> LENGTH: 9
<212> TYPE: DNA
<213> ORGANISM: Artificial Sequence
<220> FEATURE:
<223> OTHER INFORMATION: Restriction site sequence

<400> SEQUENCE: 11 ctggaattc                                                            9

<210> SEQ ID NO 12
<211> LENGTH: 13
<212> TYPE: DNA
<213> ORGANISM: Artificial Sequence
<220> FEATURE:
<223> OTHER INFORMATION: Restriction site sequence

<400> SEQUENCE: 12
gaattccagc aca                                                      13

<210> SEQ ID NO 13
<211> LENGTH: 13
<212> TYPE: DNA
<213> ORGANISM: Artificial Sequence
<220> FEATURE:
<223> OTHER INFORMATION: Restriction site sequence

<400> SEQUENCE: 13
gaattccacc aca                                                      13

<210> SEQ ID NO 14
<211> LENGTH: 9
<212> TYPE: DNA
<213> ORGANISM: Artificial Sequence
```

-continued

```
<220> FEATURE:
<223> OTHER INFORMATION: Restriction site sequence

<400> SEQUENCE: 14 gtggaattc                                                                9
```